United States Patent [19]

Garland

[11] Patent Number: 5,207,574
[45] Date of Patent: May 4, 1993

[54] DENTAL MODEL AND PROCESS OF MAKING SAME

[76] Inventor: James K. Garland, 3255 E. Seven Springs Dr., Sandy, Utah 84092

[21] Appl. No.: 620,706

[22] Filed: Dec. 3, 1990

[51] Int. Cl.$^5$ .................... A61C 19/00; A61C 11/00
[52] U.S. Cl. .................................... 433/74; 433/58; 433/213
[58] Field of Search ............ 433/74, 34, 213, 57, 433/58

[56] References Cited

U.S. PATENT DOCUMENTS

| | | | |
|---|---|---|---|
| 1,341,191 | 5/1920 | Nakahara | 433/58 |
| 1,471,019 | 10/1923 | Wilson | 433/58 |
| 1,644,106 | 10/1927 | Bridge | 433/57 |
| 2,851,728 | 9/1958 | Spalten et al. | 433/74 |
| 3,226,827 | 1/1966 | Spalten | 433/74 |
| 3,436,827 | 4/1969 | Dew | 433/34 |
| 3,702,027 | 11/1972 | Marshall et al. | 433/34 |
| 4,300,884 | 11/1981 | Camacho | 433/74 |
| 4,443,192 | 4/1984 | Blitz | 433/74 |
| 4,459,110 | 7/1984 | Jackson | 433/74 |
| 4,720,265 | 1/1988 | Jacobi | 433/74 |
| 4,767,330 | 8/1988 | Burger | 433/74 |
| 4,840,565 | 6/1989 | Poveromo | 433/74 |
| 4,846,684 | 7/1989 | Oestreich | 433/213 |

*Primary Examiner*—Gene Mancene
*Assistant Examiner*—Cindy A. Cherichetti
*Attorney, Agent, or Firm*—Terry M. Crellin

[57] ABSTRACT

A dental model and articulation system are disclosed. The dental model comprises cast mold material formed around an elongate pin or rod. A longitudinal, tapered pin or rod is embedded in the model during pouring of the casting material. The pin or rod extends longitudinally through the base of the model beneath the teeth impressions of the model. The longitudinal axis of the pin or rod lies in general parallel alignment with the line of teeth in the model. The pin or rod can be removed from the model, and the model can be cut into several sections or dies. These sections or dies can then be reassembled back on the pin or rod in the precise, true relationship that existed in the model prior to the model being cut into sections. The extending ends of the pins or rods can be removably attached to a flexible member such that models of the upper teeth and lower teeth of a person's jaws can be moved in lateral or protrusive movement and back to centric occlusion.

18 Claims, 2 Drawing Sheets

DENTAL MODEL AND PROCESS OF MAKING SAME

BACKGROUND OF THE INVENTION

1. Field of the Invention

The present invention relates generally to dental models and more particularly to a novel model having a single, elongate, tapered pin that extends longitudinally through the base of the model beneath the teeth impressions of the model, whereby the pin can be removed from the model so that the model can be cut into isolated sections, and the sections can then be reassembled on the pin in their exact, precise relationship as in the model prior to cutting of the isolated sections. The present invention further relates to a method of making the novel dental model and to a novel articulation system for use with models of lower and upper teeth of a person's jaw.

2. State of the Art

In order to fabricate a dental prosthetic, such as a crown, inlay, bridge etc., a negative impression of a patient's mouth is taken using an impression material, and a reproduction of the impression is made as a model in the dental laboratory. Since the reproduction is a solid, positive model of the gums and at least several adjacent teeth in the mouth, it is necessary to isolate reproductions or dies of the individual tooth or teeth that have been prepared by the dentist to receive a restorative prosthetic.

The isolation of the desired tooth or teeth in the model is generally accomplished by sawing or cutting the solid, cast model into separate parts, i.e., the dies, with a separate die being cut for each tooth that is to receive a restorative prosthetic. Each desired die then consists of an isolated tooth of the model. Typically, the model will contain at least about 3 teeth, and cuts are made so as to isolate at least one of the teeth from the others.

It is essential during the construction of the prosthetic to reassemble the teeth dies back into the original model. When reassembled, the teeth must be located in as true as possible relationship to each other in the reassembled model as they were in the original, uncut model. To accomplish this, the methods used in the prior art have involved a time consuming operation wherein the tooth die is cut so as to be removed from the base stone, with the base stone remaining in a single, uncut condition. Means are then provided for repositioning the cut tooth die back on the base stone in as nearly as possible true relationship to its original position.

In one method called the grid method, the dental casting material forming the model is poured into a grid box combined with the negative mold of the person's teeth and gums. The model is cut to form the separate teeth sections or dies, and the dies can then be repositioned on the grid. This method has the serious disadvantage that getting the dies to relocate to precise position is difficult and time consuming because of debris lodging in the grids.

Several methods have been used in the prior art that utilize various types of dowel pins, each of which is secured to an individual die, for relocating the die back on the base stone. The methods of securing the dowel pins to the individual tooth die have been complicated and labor intensive. In one method, a dowel pin is incorporated into the cast material of the dental model in such a manner that when the tooth die is cut, the dowel pin remains in the tooth die and leaves a receptacle in the base stone so that the die can be reassembled to the base stone by inserting the projecting portion of the dowel pin of the tooth die into the respective receptacle in the base stone. In a second method, the entire, solid, dental model is first made and then holes are drilled above the individual prepared tooth areas or dies to receive individual dowel pins which are inserted and glued into the drilled holes. In either method, the dowel pins allow the tooth die to be removed from the mold and then relocated in the mold.

The dowels have in the past been shaped to alleviate rotational movement of the die relative to the axis of the dowel when the dowel is inserted into the receptacle in the base stone. However, precautions must still be rigidly adhered to in using the dental models having dies incorporating individual dowels. Rotation of the die relative to the dowel must be avoided. In addition, movement of the die in a fulcrum or pivoting effect, as well as up and down movement, must carefully be guarded against. Another serious disadvantage involves the extensive labor required in making the models utilizing a dowel for each individual die. It would be highly desirable to provide a dental model system that does not require a dowel pin for each removable tooth die, and that does not require excessive labor to make the model. There is a long felt need for a model in which the dies can be quickly and easily removed from the model and then just as quickly and easily reassembled into exact, precise relocation relative to the other teeth of the model, with no special precautions needed to prevent undesired movement of the individual dies in the reassembled mold.

BRIEF DESCRIPTION OF THE INVENTION

In accordance with the present invention, a novel dental model and a novel articulation system used in combination with the dental model are provided. The dental model and the articulation system are both designed to be highly effective, easy to use and inexpensive. In addition, and of principal significance, the dental model and articulation system are capable of saving considerable labor time of the specialist in making of the model as well as in using the model and articulation system in constructing a dental prosthetic.

In one aspect of the invention, the principal component comprises a novel dental model. The model is made from conventional impressions or negative molds of a person's teeth and gums. During the pouring and casting of the dental casting material in the negative mold, a longitudinal, tapered pin or rod is embedded in the casting material The pin or rod extends longitudinally through the base of the model beneath the teeth impressions of the model, with the pin or rod being positioned so that the longitudinal axis of the pin or rod lies in general parallel alignment with the line of the teeth in the negative mold. The pin or rod is advantageously spaced from the teeth impressions in the base portion of the model that is being poured. The longitudinal axis of the pin or rod need not be in exact parallel alignment with the line of teeth, but it must generally follow the same general alignment as the line of the teeth in the negative mold. In essence, the pin or rod must extend along a longitudinal direction through the model that is being made such that the pin or rod extends beneath the teeth in the model.

As will be described fully hereinafter, after the model has been poured and the casting material has set into a hard cast model, the model is removed from the negative mold. The longitudinal pin or rod is withdrawn and removed from the model, and the desired dies are sectioned from the model, i.e., the model is cut into the desired sections to isolate one or more teeth for which a dental prosthesis is to be made. These sections can be reassembled on the pin or rod to recreate the precise, true relationship of the teeth in the dental model prior to the cutting of the model into sections. This allows the prosthetic device being constructed to be formed to not only fit exactly the remnant of the tooth that has been prepared by the dentist but to also precisely conform with adjacent teeth of the patient's mouth.

In another unique aspect of the invention, the end of the pin or rod that extends from the dental model is made to be quickly attached to and detached from a novel articulation system that allows the dental prosthetic device that is being constructed to be formed to conform and match the teeth in the opposite row of teeth for proper occlusion of the teeth as the patient bites and chews. The articulation system comprises a flex member which can be made of plastic, rubber or a spring member such as a coiled spring. The respective models are attached by way of the pin or rod of each model to opposite ends of the flex member. The models can then be moved in lateral or protrusive movements and back to centric occlusion to check proper mating of the prosthetic device with the tooth and teeth that it occludes during biting and chewing.

Additional objects and features of the invention will become apparent from the following detailed description, taken together with the accompanying drawings.

THE DRAWINGS

Preferred embodiments of the present invention representing the best mode presently contemplated of carrying out the invention are illustrated in the accompanying drawings in which.

Figure 4:
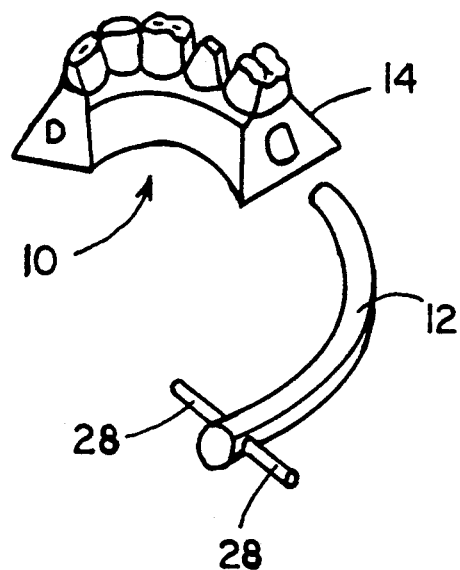
Figure 6:
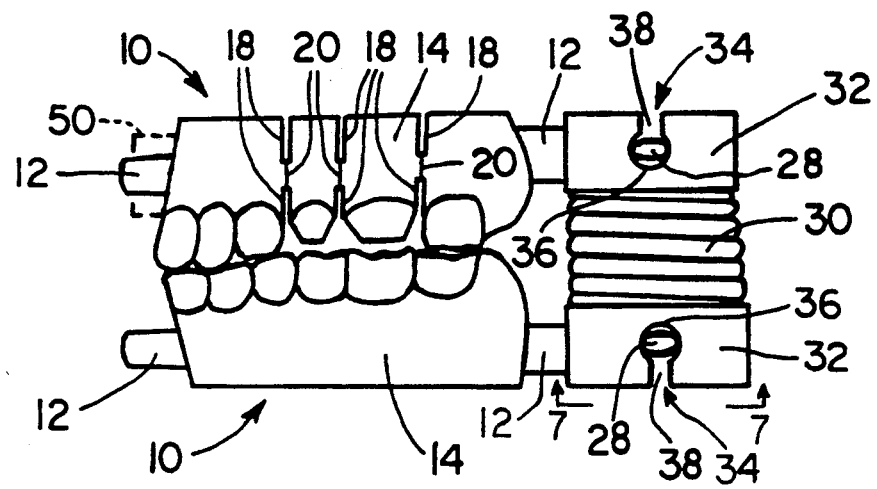
Figure 5:
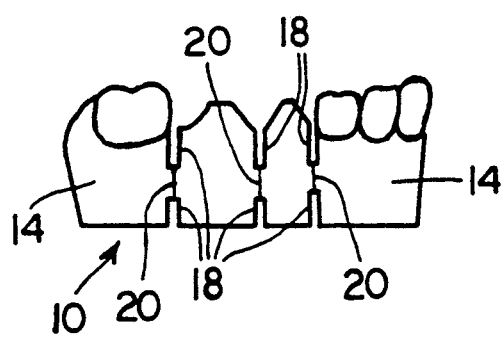
Figure 7:
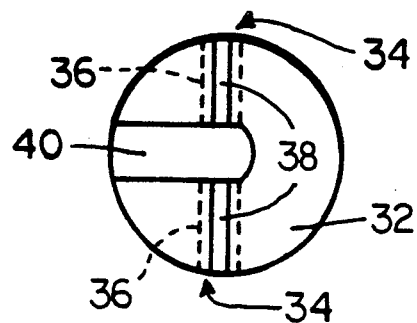

FIGS. 3(a) through 3(d) are four cross sections of four different shapes that the pin or rod of the present invention might take;

FIG. 4 is an exploded pictorial view of a novel dental model in accordance with the invention in which the teeth are front teeth which are aligned along a curved line or path and the pin or rod is curved along its longitudinal length in the same approximate curvature as that of the curved alignment of the teeth in the model;

FIG. 5 is a side elevation of a dental model in accordance with the invention in which the pin or rod has been removed and the model sawed to form sections or dies;

FIG. 6 is a side elevation of two dental models in accordance with the invention that are removably attached to a novel articulation system in accordance with the present invention; and FIG. 7 is an end view of one of the end caps of the articulation system of FIG. 6 as taken along line 7—7 of FIG. 6.

DETAILED DESCRIPTION OF THE ILLUSTRATED EMBODIMENTS

Referring now to the drawings, a novel dental model is shown generally by the reference number 10. The novel dental model comprises an elongate, tapered pin 12 that is embedded in a cast mold material 14. The cast material 14 is formed around the longitudinal side of the pin 12 to encapsulate at least the central portion of the elongate pin 12. At least one end of the pin 12 extends from an end of the cast mold material, and the second end of the pin may or may not extend from the cast mold material.

An impression of at least two adjacent teeth of a person is formed in the exterior surface of the cast mold material 14. The dental model is advantageously formed by pouring a first layer of dental casting material into a negative mold (not shown in the drawings) of a person's teeth and gums. The dental casting material is of the type that is capable of curing into a solid. An example of a dental casting material is plaster. The elongate, tapered pin 12 is positioned on the first layer of dental casting material, and additional dental casting material is then poured around the elongate pin 12 to encapsulate at least the central portion of the pin 12 so that the central portion of the pin 12 is positioned adjacent to the teeth impressions of the mold. At least one end of the pin, and preferably both ends, extend from the dental casting material. As mentioned previously, both ends may extend from the dental casting. The pin 12 passes generally through what is referred to as the base of the stone of the model, or at least between the base and the teeth portion of the model. In the model of the present invention, the teeth portion and the base portion are cast as an integral piece.

Figure 1:
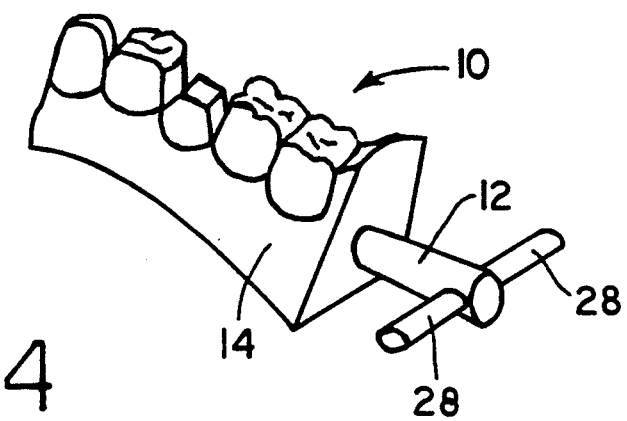
FIG. 1 is a pictorial representation of a novel dental model of the present invention shown as the model is removed from the negative mold and prior to sectioning of the model into separate dies.

After pouring, the dental casting material is allowed to cure into a solid model 10 of the teeth and gums of the mold, with the model having the pin embedded therein. The model 10 containing the embedded pin 12 is then removed from the negative mold and the model at this stage of development is shown in FIG. 1 of the drawings.

Following removal of the model 10 from the negative mold, the pin 12 is pulled longitudinally from the cast mold material 14 in preparation of cutting the cast mold material 14 into sections. The pin 12 is tapered from its one end to the other and can be readily disengaged and pulled from the model 10. The pin 12 could be reinserted into the model 10 if so desired, but it is advantageous to cut the model 10 into sections or dies before reassembling the model 10 on the pin 12.

In preparing a prosthetic device, it is necessary to isolate a section of the cast model 10 having an isolated tooth associated therewith. Such a section is generally referred to as a die. The sections or dies are formed so that they can be reassembled on the pin 12 to recreate the dental model 10 having the teeth thereof situated adjacent each other in true relationship of the dental model 10 prior to removal of the pin and cutting of the model into sections.

The sections or dies are preferably created by sawing cuts 18 partially through the solid cast material of the model 10 at desired positions relative to the teeth in the model 10 as best shown in FIG. 5. The saw cuts 18 do not extend completely through the cast material of the model 10. The portion of the cast material is then snap broken at each of the cuts 18 to form separate sections of the model 10. By snap breaking the cast material of the model 10 at the cuts 18, the sections or dies can be reassembled in true relationship on the pin 12. The cuts 18 are preferably formed in pairs, with the first cut of each pair extending downwardly from the teeth side of the model and the second cut of each pair extending upwardly from the side on the model opposite the teeth in a direction toward the first cut. The snap breaking then occurs between the inner ends of the first and second cuts of each pair of cuts 18 as shown by reference number 20 in FIG. 5.

When both ends of the tapered pin or rod 12 extend from the model as shown in FIG. 6, the separate dies can fall from the smaller end of the pin or rod 12 if the model is inverted so that the smaller end of the pin or rod 12 is pointed downwardly. A simple retainer sleeve 50 as shown in phantom in FIG. 6 can be slid on the extending smaller end of the pin or rod 12 to hold the dies on the pin or rod 12. The retainer sleeve 50 is advantageously made of an elastomeric material that grips the extending end of the pin or rod 12. The retainer sleeve 50 could be in the form of a cap that completely covers the extending end of the pin or rod 12.

Figure 2:
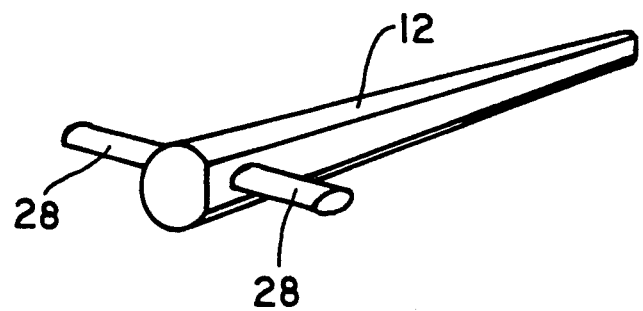
FIG. 2 is a pictorial view of the pin or rod of the present invention shown in isolation.
Figure 3:
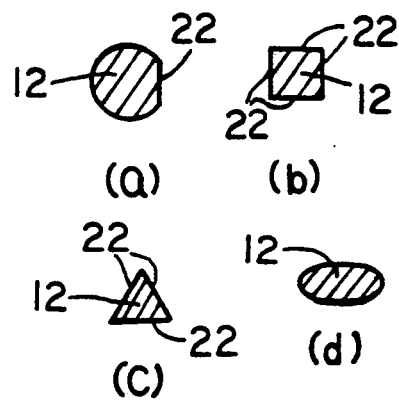

In the dental model 10 of the present invention, the elongate pin 12 has an elongate surface characteristic such that the cast mold material formed on the pin 12 cannot rotate relative to the longitudinal axis of the pin 12 when the mold material is in proper position on the pin. Advantageously, the elongate surface characteristic comprises at least one flat side 22 formed along the length of the pin 12. As shown in FIGS. 2 and 3a, the pin 12 can have a generally circular cross-sectional shape with a flat side 22 formed along one side thereof. As shown in FIGS. 3b and 3c, the pin 12 could also have a cross-sectional shape of a triangle or rectangle wherein there are three or four flat sides 22. In addition, the pin 12 can be formed with a cross section having the shape of an oval as shown in FIG. 3d.

In making prosthetic devices for the back teeth, i.e., the bicuspids and molars, the teeth being modeled are aligned in a generally straight line, and the model 10 which is made of the teeth will have a generally straight longitudinal shape as shown in FIG. 1 When making prosthetic devices for front teeth, i.e., incisors and canines, the teeth being modeled are aligned along a curved path or line, and the model 10 which is made of the teeth will have a generally curved longitudinal shape as shown in FIG. 4. In the model 10 having a curved longitudinal shape, the pin 12 is curved along its longitudinal length to approximate the curvature of the curved alignment of the teeth in the model 10.

It has been found that the curved pin 12 as shown in FIG. 4 can be removed from the cast model 10 of FIG. 4 just as readily as can the straight pin 12 be removed from the cast model 10 of FIG. 1. The curved cast model 10 of FIG. 4 can then be sectioned to isolate a desired tooth, and the sections can be reassembled on the curved pin 12 of FIG. 4 in the same manner as previously described for the model 10 having a straight pin 12.

In making a dental prosthetic for even a single tooth, a model is made of the row of teeth containing the tooth for which the prosthetic device is being made. It is further advantageous to make a model of the teeth in the other jaw which occlude the row of teeth containing the tooth for which the prosthetic device is being made. This allows the fitting of the new prosthetic device to the teeth adjacent to the new prosthetic device in the row of teeth in which the prosthetic device is a part as well as the occlusion of the new prosthetic device with teeth in the opposing jaw. Thus, there are two dental models made including two tapered pins 12 with cast mold materials formed about each of the respective pins to form separate impressions or models 10 of corresponding upper and lower teeth of a person's jaws. One end of each of the pins 12 extends from the cast mold material associated therewith, and a novel articulation system is provided for checking the movement of the prosthetic device relative to the teeth in the opposite jaw.

In one form of the articulation system, a pair of pins 12 can be permanently affixed to a resilient, connecting member, such that the pins 12 are held in spaced apart positions being essentially parallel with each other. The models are formed about each of the pins so that the teeth of the models meet in centric occlusion. The resilient nature of the connecting member allows the two models to be moved in lateral and protrusive motions for checking proper mating of the teeth in the lower and upper models.

A particularly preferred articulation system in accordance with the present invention comprises a flexible, resilient element having upper and lower ends. Means are provided for removably attaching respective ends of the pins 12 to the respective upper and lower ends of the flexible element rather than having the pins 12 permanently affixed to the flexible element. The flexible, resilient element then forms an articulation member that allows the two impressions or models to move in lateral or protrusive movements and then back into centric occlusion.

As best shown in FIG. 5, the flexible, resilient element preferably comprises a coil wound spring 30, with means for removably attaching the respective one ends of the pins 12 to the upper and lower ends of the coil spring 30. As illustrated in FIGS. 6 and 7, the means for attaching the ends of the pins 12 to the coil spring 30 comprises cap members 32 attached to the upper and lower ends of the coil spring 30, with means for releasably attaching the one ends of the pins 12 to the cap members 32.

As illustrated, the caps 32 have snap in receptacles 34 that accept ears 28 on the ends of the pins 12. The receptacles 34 in the caps 32 may comprise a circular opening 36 extending through the cap 32 from ones side to the other. A slot 38 connects the openings 36 with the outer ends of each of the caps 32. The slot 38 has a width which is less than the diameter of the opening 36.

The ears 28 on each of the ends of the pins 12 have an oval cross-sectional shape, with the minor axis of the oval being the same dimension or nearly the same dimension as the width of the slot 38. The major axis of the oval of the ears 28 is the same dimension or nearly the same dimension as the diameter of the opening 36. The ears 28 can be introduced into the opening 36 through the slot 38 when the major or longer axis of the oval ears 28 points downwardly through the slot 38 into the opening 36. The ears 28 are then retained firmly in the opening 36 when they are rotated so that the major or longer axis of the oval ears 28 engages the opening 36. A cut out keyway 40 is provided in the outer ends of each cap 32 to receive the pin 12 when the dental model 10 and pin 12 are rotated so as to extend outwardly from the side of the cap 32 as shown in FIG. 6. The dental models can easily and quickly be removed from the caps 32 by rotating the models 10 and pins 12 into axial alignment with the caps 32 and pulling the ears 28 from the openings 36 through the slots 38 in each of the caps 32.

Although preferred embodiments of the present invention have been illustrated and described, it is to be understood that the present disclosure is made by way of example and that various other embodiments are possible without departing from the subject matter coming within the scope of the following claims, which subject matter is regarded as the invention.

I claim:

1. A dental model of a patient's teeth for use in preparing a dental prosthetic for the patient's teeth, said dental model comprising
    an elongate, tapered pin;
    a mold material cast around the longitudinal side of said pin to encapsulate at least the central portion of said elongate pin;
    an impression of at least two adjacent teeth of a person formed integrally in the exterior surface of the cast mold material;
    cuts formed partially through said cast mold material transverse of the longitudinal side of said pin; and
    breaks formed through the cast mold material at the cuts to separate the cast mold material into at least three distinct, isolated sections that are aligned in sequence with each other in a direction along the longitudinal side of said pin; and
    breaks formed through the cast mold material at the cuts to separate the cast mold material into at least three distinct, isolated sections that are aligned in sequence with each other in a direction along the longitudinal side of said pin,
    whereby the pin can be pulled longitudinally from the cast mold material to separate and isolates sections of the cast mold material from each other, and whereby the isolated sections can be reassembled by stacking the sections side-by-side in sequence on the pin to recreate the dental mode having teeth situated adjacent each other in true relationship of the dental model prior to removal of the pin and separation of the cast mold material into sections.

2. A dental model in accordance with claim 1, wherein the elongate pin has an elongate surface characteristic such that the cast mold material formed on the pin cannot rotate relative to the longitudinal axis of said pin which the mold material is in proper position on the pin.

3. A dental model in accordance with claim 2, wherein the elongate surface characteristic comprises at least one flat side formed along the length of said pin.

4. A dental model in accordance with claim 2, wherein the elongate surface characteristic comprises the pin being formed with a cross section having the shape of an oval.

5. A dental model in accordance with claim 2, wherein the pin is curved along its longitudinal length to approximate the curvature of the curved alignment of the teeth impression in the model.

6. A dental model in accordance with claim 2, wherein said dental model comprises two elongate member with cast molds formed around the longitudinal side of each of the respective elongate members to form separate impressions of corresponding upper and lower teeth of a person's jaw, and further wherein one end of each of said elongate members extends from the cast mold associated therewith, and the dental model further comprises a flexible, resilient element having upper and lower ends; and
means for attaching respective one ends of said elongate members to the respective upper and lower ends of said flexible element,
whereby the flexible, resilient element forms an articulation member that allows the two impressions to move in lateral or protrusive movements and then back into centric occlusion.

7. A dental model in accordance with claim 6, wherein the one ends of said elongate members are removably attached to the respective ends of said flexible element.

8. A dental model in accordance with claim 6, wherein the flexible, resilient element comprises a coil wound spring and the means for attaching the respective one ends of said elongated members to the upper and lower ends of the coil spring comprise cap members attached to the upper and lower ends of the coil spring, with means for releasably attaching the one ends of said elongate members to said cap members.

9. A method of making a dental mode comprising
    pouring a first layer of dental casting material into a negative mold of a person's teeth and gums;
    positioning an elongate, tapered pin on the first layer of dental casting material;
    continuing to pour dental casting material around the elongate pin to encapsulate at least the central portion of said pin that is positioned above the teeth impressions of said mold, but allowing at least one end of said pin to extend from the dental casting material;
    allowing the dental casting material to cure into an integral solid model of the teeth and gums of the mold, with said model having said pin embedded therein;
    removing the model containing the embedded pin from said negative mold;
    withdrawing the pin from said model;
    sawing cuts partially through the solid cast material of the model at desired positions relative to the teeth in the model;
    snap breaking the cast material of the model at each of the cuts to form separate sections of the model; and
    reassembling the sections by stacking the section side-by-sdie on said pin.

10. The method in accordance with claim 9, wherein the cuts are formed in pairs, with the first cut of each pair extending downwardly from the teeth side of the model and the second cut of each pair extending upwardly from the side on the model opposite the teeth in a direction toward the first cut, and the snap breaking occurs between the inner ends of the first and second cuts of each pair of cuts.

11. A method in accordance with claim 9, wherein the elongate pin has an elongate surface characteristic such that the cast mold material formed on the pin cannot rotate relative to the longitudinal axis of said pin when the mold material is in proper position on the pin.

12. A method in accordance with claim 11, wherein the elongate surface characteristic comprises at least one flat side formed along the length of said pin.

13. A method in accordance with claim 11, wherein the elongate surface characteristic comprises the pin being formed with a cross section having the shape of an oval.

14. A method in accordance with claim 9, wherein the pin is curved of the curved alignment of the teeth impressions in the model.

15. A method of making a dental model comprising
pouring first layers of dental casting material into a pair of negative molds corresponding to a person's upper and lower teeth and gums;
positioning an elongate, tapered pin on the respective first layers of dental casting material;
continuing to pour dental casting material around each of the elongate pins to encapsulate at least the central portion of each said pin that is positioned above the teeth impressions of the corresponding mold, but allowing at least one end of each said pin to extend from the dental casting material;
allowing the dental casting material in each mold to cure into integral solid models of the teeth and gums of the respective molds, with each of said models having a respective pin embedded therein;
removing the models containing the respective embedded pins from said negative molds;
withdrawing the pins from said models;
sawing cuts partially through the solid cast material of each of the models at desired positions relative to the teeth in the models;
snap breaking the cast material of each of the models at each of the cuts to form separate sections of the respective models;
reassembling the sections of each respective model on a corresponding pin; and
respective one ends of each pin of said models are removably attached to opposite ends of a flexible, resilient element, whereby the flexible, resilient element forms an articulation member that allows the two models of the teeth and gums to move in lateral or protrusive movements and then back into centric occlusion.

16. A method in accordance with claim 15, wherein respective one ends of each pin of said models are removably attached to the opposite ends of the flexible, resilient element.

17. A method in accordance with claim 15, wherein flexible, resilient element comprises a coil wound spring and the respective one ends of said pins are removably attached to the opposite ends of the coil spring.

18. A method in accordance with claim 17, wherein cap members are connected to the opposite ends of the coil spring, and the one ends of said pins are removably attached to the respective cap members.

* * * * *